US006613319B2

(12) United States Patent
Leiden

(10) Patent No.: US 6,613,319 B2
(45) Date of Patent: *Sep. 2, 2003

(54) LONG-TERM EXPRESSION OF ERYTHROPOIETIN AND GROWTH HORMONE BY TRANSFORMING MUSCLE CELLS

(75) Inventor: Jeffrey M. Leiden, Chicago, IL (US)

(73) Assignee: Arch Development Corporation, Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/091,134

(22) Filed: Jun. 23, 1998

(65) Prior Publication Data

US 2002/0122788 A1 Sep. 5, 2002

Related U.S. Application Data

(60) Provisional application No. 60/024,511, filed on Aug. 23, 1996.

(51) Int. Cl.[7] .......................... A01N 63/00; A01N 43/04; A61K 48/00; A61K 31/70; C12N 15/63
(52) U.S. Cl. .................. 424/93.2; 424/93.1; 424/93.21; 424/93.6; 424/93.7; 435/320.1; 435/455; 514/44
(58) Field of Search .............................. 424/93.1, 93.2, 424/93.21, 93.6, 93.7; 435/320.1, 455; 514/44

(56) References Cited

U.S. PATENT DOCUMENTS

| 5,580,859 A | 12/1996 | Felgner et al. ................. 514/44 |
| 5,693,622 A | 12/1997 | Wolff et al. .................... 514/44 |
| 5,858,351 A | 1/1999 | Podsakoff et al. ......... 424/93.2 |

FOREIGN PATENT DOCUMENTS

| WO | WO 95/13376 | * 5/1995 |

OTHER PUBLICATIONS

Crystal RG (1995) Transfer of genes to humans: Early lessons and obstacles to success. Science 270: 404–410.*
Deonarain MP (1998) Ligand–targeted receptor–mediated vectors for gene delivery, Exp. Opin. Ther. Patents 8(1): 53–69.*
Marshall E (1995) Gene therapy's growing pains. Science 269: 1050–1055.*
Miller et al. (1995) Targeted vectors for gene therapy. FASEB J. 9: 190–199.*
Naffakh et al. (1996) Long–term secretion of therapeutic proteins from genetically modified skeletal muscles. Human Gene Therapy 7:11–21.*

Osborne et al. Gene therapy for long–term expression in erythropoietin in rats. Proc. Natl. Acad. Sci. USA 92: 8055–8058, Aug. 1995.*
Raz et al. Systemic immunological effects of cytokine genes injected into skeletal muscle. Proc. Natl. Acad. Sci. USA 90: 4523–4527, May 1993.*
Tripathy et al. Immune responses to transgene–encoded proteins limit the stability of gene expression after injection of replication–defective adenovirus vector. Nature Medicine 2(5): 545–550, May 1996.*
Dhawan et al. Systemic delivery of human growth hormone by injection of genetically engineered myoblasts. Science 254: 1509–1512, Dec. 1991.*
Orkin and Motulsky. Report and recommendations of the panel to assess the NIH investment in research on gene therapy, Dec. 1995.*
Friedmann, T. Overcoming the obstacles to gene therapy. Sci. Am. Jun. 1997. pp. 96–101, Jun. 1997.*
Tripathy et al. Stable delivery of physiologic levels of recombinant erythropoietin to the systemic circulation by intramuscular injection of replication–defective adenovirus. Proc. Natl. Acad. Sci. USA 91: 11557–11561, Nov. 1994.*
Verma et al. Gene therapy—promises, problems and prospects. Nature 389: 239–242, Sep. 1997.*
Tripathy, et al., "Immune responses to transgene–encoded proteins limit the stability of gene expression after injection of replication–defective adenovirus vectors", Nature Med. 2:545–550 (1996).
Tripathy et al., "Stable delivery of physiologic levels of recombinant erythropoietin to the systemic circulation by intramuscular injection of replication–defective adenovirus", Proc. Natl. Acad. Sci. USA 91:11557–11561 (1994).
Barr et al., "Efficient catheter–mediated gene transfer into the heart using replication–defective adenovirus", Gene Ther. 1:51–58 (1994).
Barr et al., "Strain related variations in adenovirally mediated transgene expression from mouse hepatocytes in vivo: comparisons between immunocompetent and immunodeficient inbred strains", Gene Ther. 2:151–155 (1995).
Kass et al., "The impact of developmental stage, route of administration and the immune system on adenovirus–mediated gene transfer", Gene Ther. 1:395–402 (1994).

(List continued on next page.)

*Primary Examiner*—Anne-Marie Falk
(74) *Attorney, Agent, or Firm*—Hale and Dorr LLP

(57) ABSTRACT

A process for increasing the circulating levels of gene products in a primate for extended period of time is provided. In accordance with that process, muscle cells of the mammal are transformed with an expression vector that contains a polynucleotide that encodes the gene product and which vector drives expression in the muscle.

24 Claims, No Drawings

OTHER PUBLICATIONS

Mastrangeli et al., "Sero–Switch" Adenovirus–Mediated In Vivo Gene Transfer: Circumvention of Anti–Adenovirus Humoral Immune Defenses Against Repeat Adenovirus Vector Administration by Changing the Adenovirus Serotype, Hum. Gene Ther. 7:79–87 (1996).

Yang et al., "Immune responses to viral antigens versus transgene product in the elimination of recombinant adenovirus–infected hepatocytes in vivo", Gene Ther. 3:137–144 (1996).

Brody et al., "Acute Responses of Non–Human Primates to Airway Delivery of an Adenovirus Vector Containing the Human Cystic Fibrosis Transmembrane Conductance Regulator cDNA", Human Gene Ther. 5:821–836 (1994).

Yang et al., "Cellular immunity to viral antigens limits E1–deleted adenoviruses for gene therapy", Proc. Natl. Acad. Sci USA 91:4407–4411 (1994).

Yang et al., Clearance of Adenovirus–Infected Hepatocytes by MHC Class 1–Restricted CD4$^+$CTLs in Vivo, J. Immunol. 155:2564–2570 (1995).

Dhawan et al., "Systemic Delivery of Human Growth Hormone by Injection of Genetically Engineered Myoblasts", Science 254:1509–1512 (1991).

Barr and Leiden, "Systemic Delivery of Recombinant Proteins by Genetically Modified Myoblasts", Science 254: 1507–1509 (1991).

Yao, S. and Kurachi, K., "Expression of human factor IX in mice after injection of genetically modified myoblasts", PNAS USA 9:3357–3361 (1992).

Partridge et al., "Conversion of mdx myofibres from dystrophin–negative to –positive by injection of normal myoblasts", Nature 337:176–179 (1989).

Dai et al., "Gene therapy via primary myoblasts: Long–term expression of factor IX protein following transplantation in vivo", PNAS USA 89: 10892–5 (1992).

Hamamori et al., "Persistent Erythropoiesis by Myoblast transfer of Erythropoietin cDNA", Hum. Gene Ther. 5:1349–1356 (1994).

Hamamori et al., "Myoblast Transfer of Human Erythropoietin Gene in a Mouse Model of Renal Failure", J. Clin. Invest. 95:1808–1813 (1995).

Kay et al., "In vivo hepatic gene therapy: Complete albeit transient correction of factor IX deficiency in hemophilia B dogs", PNAS USA 91:2353–7 (1994).

Rosenfeld, et al., "Adenovirus–Mediated Transfer of a Recombinant α1–Antitrypsin Gene to the Lung Epithelium in Vivo", Science 252:431–434 (1991).

Lemarchand et al., "Adenovirus–mediated transfer of a recombinant human α1–antitrypsin cDNA to human endothelial cells", PNAS USA 89:6482–6 (1992).

Vincent et al., "Long–term correction of mouse dystrophic degeneration by adenovirus–mediated transfer of a minidystrophin gene", Nat. Genet. 5:130–4 (1993).

Engelhardt et al., "Prolonged Transgene Expression in Cotton Rat Lung with Recombinant Adenoviruses Defective in E2a", Hum. Gene Ther. 5:1217–29 (1994).

Mendell et al., "Myoblast Transfer in the Treatment of Duchenne's Muscular Dystrophy", N. Engl. J. Med. 333:832–8 (1995).

Morgan, J.E., "Cell and Gene Therapy in Duchenne Muscular Dystrophy", Hum. Gene Ther. 5:165–73 (1994).

Dai et al., "Cellular and humoral immune responses to adenoviral vectors containing factor IX gene: Tolerization of factor IX and vector antigens allows for long–term expression", PNAS USA 92:1401–5 (1995).

Yang et al., "Cellular and Humoral Immune Responses to Viral Antigens Create Barriers to Lung–Directed Gene Therapy with Recombinant Adenoviruses", J. Virol. 69:2004–15 (1995).

Yang et al., "MHC Class 1–Restricted Cytotoxic T Lymphocytes to Viral Antigens Destroy Hepatocytes in Mice Infected with E1–Deleted Recombinant Adenoviruses", Immunity 1:433–42 (1994).

Wolff et al., "Direct Gene Transfer into Mouse Muscle in Vivo", Science 247:1465–1468 (1990).

Wolff et al., "Long–term persistence of plasmid DNA and foreign gene expression in mouse muscle", Hum. Mol. Gen. 1:363–9 (1992).

Manthorpe et al., "Gene Therapy by Intramuscular Injection of Plasmid DNA: Studies on Firefly Luciferase Gene Expression in Mice", Hum. Gene Ther. 4:419–31 (1993).

Setoguchi, et al., Stimulation of Erythropoiesis by In Vivo Gene Therapy: Physiologic Consequences of Transfer of the Human Erythropoietin Gene to Experimental Animals Using an Adenovirus Vector, Blood 84:2946 (1994).

* cited by examiner

SEQUENCE LISTING

<160> NUMBER OF SEQ ID NOS: 8

<210> SEQ ID NO 1
<211> LENGTH: 31
<212> TYPE: DNA
<213> ORGANISM: Artificial Sequence
<220> FEATURE:
<223> OTHER INFORMATION: primer

<400> SEQUENCE: 1
ggggtcgacg gcggggagat ggggtgccc g                         31

<210> SEQ ID NO 2
<211> LENGTH: 32
<212> TYPE: DNA
<213> ORGANISM: Artificial Sequence
<220> FEATURE:
<223> OTHER INFORMATION: primer

<400> SEQUENCE: 2
gggagatcta gttcacctgt ccctctcct gc                        32

<210> SEQ ID NO 3
<211> LENGTH: 18
<212> TYPE: DNA
<213> ORGANISM: Artificial Sequence
<220> FEATURE:
<223> OTHER INFORMATION: primer

<400> SEQUENCE: 3
ccagaccccg aagcatgg                                       18

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
ggaagactta aggcagcg                                       18

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
gaagtcaggc tacgtagacc actg                                24

-continued

```
<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gtctgagcag tactcgttgc                                            20

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7 gggggatcc gcacctggtc atctgtcc                                    28

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
gggaagcttc ccggccaggc gcggagatgg                                 30
```

LONG-TERM EXPRESSION OF ERYTHROPOIETIN AND GROWTH HORMONE BY TRANSFORMING MUSCLE CELLS

CROSS-REFERENCE TO RELATED APPLICATION

This application is a continuation in part of U.S. Provisional Patent Application Ser. No. 60/024,511, filed Aug. 23, 1996, the disclosure of which is incorporated herein by reference.

TECHNICAL FIELD OF THE INVENTION

The field of this invention is gene expression. More particularly, this invention pertains to a process for increasing the circulating levels of gene products over an extended period of time.

BACKGROUND OF THE INVENTION

A large number of inherited and acquired serum protein deficiencies including hemophilia A, diabetes mellitus and the erythropoietin-responsive anemias are currently treated by repeated intravenous or subcutaneous injections of purified or recombinant proteins. Although largely effective, such therapies are both expensive and inconvenient. Moreover, in diseases such as hemophilia A, there is not sufficient recombinant protein available to allow a comprehensive program of prophylactic therapy. Given these problems, there has been considerable interest in developing novel gene-based therapies for such serum protein deficiencies. An initial series of studies demonstrated that skeletal myoblasts genetically modified in vitro could be reimplanted by intramuscular injection and would subsequently produce stable, physiological levels of recombinant proteins in the systemic circulation of adult immunocompetent mice. Subsequently, several groups have demonstrated the stable production of recombinant serum proteins following a single intramuscular (IM) injection of replication-defective adenovirus (RDAd) vectors. Despite these initial successes, both myoblast transplantation and IM injection of RDAd vectors have thus far been associated with problems that may preclude their widespread clinical application.

The studies reported to date have all been done on rodents such as mice. Those data may not reflect and may not be predictive of results in larger animals such as primates. It is well known in the art, for example, that physiological or therapeutic doses observed in rodents are not necessarily predictive of effective doses in larger mammals. Still further, the amount of vector needed in large mammals may preclude their utility. For example, the mass of vector needed in primates may be so large that their injection results in either adverse reactions to the injection (e.g., anaphylactic shock), generation of an immune response or secondary infection resulting from the use of large numbers of viral particles. Still further, the data from previous reports do not address the question of whether there is any correlation between the amount or dose of transforming vectors and increases in the levels of gene products. There continues to be a need in the art, therefore, for processes for increasing the circulating levels of gene products in large mammals such as primates.

BRIEF SUMMARY OF THE INVENTION

The present invention provides a process of increasing the circulating levels of a gene product in the blood stream of a mammal for a period of time greater than about 30 days. The process includes the step of transforming muscle cells of the mammal with a polynucleotide that encodes the gene product, wherein the expression vector drives long-term expression of the polynucleotide.

A preferred mammal is an animal used for food such as a cow, domesticated animals such as dogs and cats and primates. A preferred primate is a human. A process of the present invention can be used to increase circulating levels of any gene product. Exemplary such gene products are RNA molecules, single-stranded DNA molecules and polypeptides. Polypeptides are particularly preferred. Especially preferred polypeptides are polypeptide hormones such as growth hormone and erythropoietin.

A process of the present invention can use any muscle such as smooth muscle, cardiac muscle and skeletal muscle. Cardiac and skeletal muscle are preferred. The use of skeletal muscle is most preferred.

Any suitable expression vector can be used in the present process. Exemplary and preferred such vectors are plasmids and replication defective adenoviral vectors. The muscle cells can be transformed either in vivo or ex vivo. When transformed in vivo, the expression vector is directly injected into a muscle mass of the mammal. When transformed ex vivo, muscle cells are removed from the mammal, transformed ex vivo and the transformed muscle cells reimplanted into the mammal.

A process of the present invention is useful for increasing the circulating levels of gene products over an extended period time. Using a process of this invention, those levels can be increased for periods of time ranging from greater than about 60, 90 or 120 days and even for as long as one year.

The safety and efficacy of IM injection of adenoviral vectors encoding Epo in both mice and non-human primates has been determined. In an initial series of experiments, the relationship between the dose of vector injected and the corresponding elevations in serum Epo levels and hematocrits in both species were studied. The results demonstrated that there is a threshold dose in both mice and monkeys (approximately $2.5–8\times10^7$ pfu/gm body weight) that is required to obtain long-term Epo expression and polycythemia. A single IM injection of mice with $10^9$ pfu of vector resulted in elevations in hematocrits from control values of 49% to treated values of 81% which were stable for more than one year. Similarly, a single IM injection of a monkey with $4\times10^{11}$ pfu of an adenoviral vector encoding simian Epo (AdsEpo) resulted in elevations of hematocrits from control levels of 40% to treated levels of ≈70% which were stable for 84 days. IM injection of monkeys with vector was determined to be safe in that no abnormalities in chest X-rays, serum chemistries, hematologic or clotting profiles (except for elevated hematocrits) or organ pathology were seen during the 84 day time course of the experiment.

DETAILED DESCRIPTION OF THE INVENTION

The present invention provides a process of increasing the circulating level of a gene product in the blood stream of a mammal for a period of time greater than about 30 days. The process includes the step of transforming muscle cells of the mammal with a polynucleotide that encodes the gene product, wherein the expression vector drives long-term expression of the polynucleotide.

As is well known in the art, gene products include polynucleotides such as DNA and RNA and polypeptides.

As is also well known in the art, those gene products can be secreted from the cells where they are made into the extracellular fluid compartment of the organism. From there, those products diffuse into the blood. The process of the present invention can be used to increase the levels of those gene products in the blood over an extended period of time. A process of this invention is particularly useful in increasing the levels of polypeptide gene products. Preferably, the polypeptide is secretory product of a cell. Exemplary such products are cytokines, colony stimulating factors, nerve growth factors and the like. Exemplary and preferred such secretory products are polypeptide or protein hormones. Such hormones are well known in the art. Exemplary polypeptide hormones are insulin, glucagon, renin, parathyroid hormone, growth hormone, erythropoietin and the like.

A process of the present invention can be used to increase the circulating level of a gene product in any mammal. The process is particularly useful in large mammals such as domestic pets, those used for food production and primates. Exemplary large mammals are dogs, cats, horses, cows, sheep, deer and pig. Exemplary primates are monkeys, apes and humans. The use of the present process in humans is particularly preferred.

The present invention discloses that increased circulating levels of gene products can be realized by transforming muscles cells of the mammal with a polynucleotide that encodes that gene product. As is well known in the art, mammals contain three types of muscle cells: smooth muscle, cardiac muscle and skeletal muscle. Any one of these muscle types can be used in a present process. Because of the accessibility of large masses of cardiac and skeletal muscle, use of these muscle types is preferred. In an especially preferred embodiment, a process of this invention uses skeletal muscle.

As used herein, the phrase "expression vector" means any vehicle for delivering an encoding polynucleotide to a cell such that the polynucleotide is expressed and a gene product is formed. Expression vectors are well known in the art. As is also well known in the art, particular vectors are especially suitable for transforming mammalian cells. For use in the present invention, plasmids and viral vectors are preferred. Exemplary viral vectors include retroviral vectors and adenoviral vectors. The vectors, especially the adenoviral vectors, are made replication defective using standard procedures well known in the art. The choice of a particular vector depends inter alia on the nature of the gene product to be produced.

Replication-defective adenoviruses represent an efficient and safe method of in vivo gene transfer. These vectors can be prepared at high titer (up to $10^{11}$ pfu/ml) and infect many replicating and non-replicating cell types in vivo. Adenoviruses are common and relatively benign human pathogens that have not been associated with persistent infections or neoplasias in humans. Wild-type adenoviruses have been used previously for human vaccination. As disclosed herein, a single IM injection of a replication-defective adenovirus encoding hEpo can be used to produce dose-dependent elevations in serum Epo levels and hematocrits which were stable over the 120 day time course of these experiments. The injected adenovirus remains localized at the site of administration and does not cause muscle pathology. Taken together, these results show that IM injection of replication-defective adenoviruses is useful for the treatment of a number of acquired and inherited human serum protein deficiencies.

Thus, in one embodiment, the expression vector is a replication defective adenoviral vector. A single IM injection of immunocompetent mice with $10^9$ to $3 \times 10^9$ plaque forming units (pfu) of an E1-and E3-deleted replication-defective adenovirus vector encoding murine Epo (AdmEpo) resulted in elevations of serum Epo levels and hematocrits from control values of approximately 45% to treated values of approximately 80% which were stable for at least 112 days (Tripathy et al., Nature Med. 2, 545–550, 1996).

As disclosed herein, an adenoviral vector, RdAd, encoding self Epo can be used to produce sustained and significant elevations in hematocrits in both mice and non-human primates. Unlike previous observations in immunocompromised SCID animals, the persistence of transgene expression in immunocompetent animals appears to be critically dependent upon the dose of virus administered, with a threshold dose of approximately $2.5–8 \times 10^7$ pfu/gm in both mice and monkeys required to obtain persistent transgene expression. From a safety standpoint, there was no evidence of pulmonary or hepatic toxicity and there was no demonstrable long term organ pathology in monkeys injected once IM with $4 \times 10^{10}–4 \times 10^{11}$ pfu of AdsEpo. Taken together, these results show that IM injection of RdAd encoding human Epo can be used to safely and effectively treat patients with Epo-responsive anemias.

Previous studies in immunocompromised animals demonstrated that IM injection of SCID mice with as little as $10^7$ pfu of Epo-encoding RdAd resulted in stable elevations in hematocrits. Increasing the viral dose to $10^8$ or $10^9$ pfu produced further increases in both serum Epo levels and hematocrits (Tripathy et al., Proc. Natl. Acad. Sci. USA, 91, 11557–11561, 1994). Thus, in SCID animals there appeared to be a simple linear relationship between the dose of virus administered and the resulting levels of Epo in the serum. The data disclosed herein in immunocompetent mice and monkeys clearly demonstrate a more complex relationship between viral dose and hematocrit. IM injection of immunocompetent mice and monkeys with low doses of virus resulted in only transient increases in hematocrit, whereas injection with higher doses of virus led to sustained elevations in serum Epo levels and hematocrits. Moreover, there appeared to be a threshold dose ($2.5–8 \times 10^7$ pfu/gm) in both species that was required for persistent transgene expression.

The observed differences between the SCID and immunocompetent animals clearly implicated the immune system as the critical determinant of these different dose-response relationships. However, there are several possible alternative mechanisms that might explain these differences. First, it is possible that the immune system eliminates a significant fraction of the Epo-expressing myocytes, independent of the dose of virus administered. In this case, initial infection of a relatively large number of myocytes might be required to end up with a sufficient number of Epo-producing cells to produce physiologic elevations in serum Epo levels. Such a model is supported by our measurements of serum Epo levels following IM injection of immunocompetent mice with AdmEpo. Peak serum Epo levels observed 1 week following viral infection subsequently declined by approximately 70% by 4 weeks after injection and then stabilized. In the animals injected with $10^8$ pfu of AdmEpo this decline resulted in serum Epo levels that fell to or below endogenous circulating Epo levels and therefore did not result in a polycythemia. In contrast, in the animals injected with $10^9$ pfu of AdmEpo, this decline still resulted in serum Epo levels that were approximately 10-fold above pre-injection levels, thereby leading to significant elevations in hematocrit.

Alternatively, it is possible that the type of immune response elicited by IM injection of the AdEpo vectors is critically dependent upon the dose of vector administered. It has recently been shown that exposure of mice to high doses of antigen leads predominantly to Th2 responses, whereas administration of lower doses of antigen leads to Th1. Therefore, it is possible that Th1 responses to the low dose of AdmEpo in the animals receiving $4\times10^{10}$ pfu of virus led to CTL-mediated elimination of virus infected cells, whereas Th2 responses to high doses of vector allowed persistence of larger numbers of Epo-producing myocytes in the animals that received $4\times10^{11}$ pfu of virus. These two mechanisms are, of course, not mutually exclusive.

The dose of virus (in pfu/gm) required to produce sustained transgene expression in mice and monkeys was quite similar. This finding indicates that it is possible to predict human doses based upon our rodent and primate data. From the mouse data, a single injection of $10^9$ pfu of AdmEpo resulted in a sustained 30 point elevation in hematocrit (from approximately 50% to 80%). Thus, it requires approximately $1.33\times10^6$ pfu/gm body weight to produce a 1 point elevation in hematocrit. For example, to produce a 15 point increase in hematocrit in a 70 kg human with Epo-responsive anemia (eg., to increase the hematocrit from 23% to 38%) it would require a single IM injection of $(1.33\times10^6$ pfu/gm)$\times15$ (% increase in hematocrit)$\times70,000$ gm$=1.4\times10^{12}$ pfu of AdhEpo. A previously reported adenoviral vector, AdhEpo, which is identical to AdmEpo and AdsEpo except that it contains the human Epo cDNA, has been shown to drive the expression and secretion of high levels of human Epo following both in vitro infection of myocytes and IM injection of SCID mice (Tripathy et al.,. Proc. Natl. Acad. Sci. USA, 91, 11557–11561, 1994).

The lack of toxicity observed in Cynomologus monkeys following IM injection of $4\times10^{11}$ pfu of AdsEpo, a dose sufficient to produce significant elevations in hematocrits, also augurs well for the safety of human gene therapy using IM injection of Epo-encoding vectors. This relative lack of toxicity as compared to previous experiments involving intravenous or inhaled routes of administration may reflect the fact that relatively little vector infects the liver or lung following IM administration. In addition, because previous experiments have demonstrated that immune responses to foreign transgenes play an important role in the inflammatory responses to RDAd-infected cells (Tripathy et al., Nature Med. 2, 545–550, 1996), the use of a self-transgene (to which the animal is tolerant) may have significantly reduced immune responses to the vector-infected cells in these animals. The present finding of excessive polycythemia in the monkey injected with $4\times10^{11}$ pfu of AdsEpo suggested that it will be essential to begin human trials with low doses of vector in order to carefully assess dose-response relationships in humans. However, the fact that injected muscle can be removed to terminate therapy adds a relative safety factor to therapies involving IM as opposed to systemic or pulmonary administration of RdAd. The use of such vectors will significantly increase the safety of adenovirus-mediated gene therapy for Epo-responsive anemias. Finally, the finding of significant levels of anti-adenoviral antibodies in mice and monkeys following a single IM injection of RdAD will likely make readministration of the vector difficult or impossible. Indeed, recent studies in mice have demonstrated that it is not possible to readminister AdsEpo to mice even 9 months after an initial IM injection. Modifications of the vector or transient immunosuppresive regiments will therefore likely be necessary to obviate this problem.

In another embodiment, the expression vector is a plasmid. The IM injection of plasmid DNA has a number of distinct advantages as compared to the use of RDAd vectors. First, plasmid DNA vectors are easier to construct, can accept large cDNA inserts, and can be prepared as pure chemical solutions without the risk of contamination with wild-type infectious particles. In addition, IM injection of adult immunocompetent animals with RDAd has been associated with immune responses that eliminate virus infected cells in 14–28 days, thereby producing only transient recombinant gene expression in vivo. Of equal importance, previous infection with wild-type adenovirus results in a neutralizing antibody response which may preclude administration of an RDAd vector. In contrast, the present disclosure demonstrates long-term Epo expression following a single IM injection of plasmid DNA even in adult immunocompetent animals. Moreover, because there were no detectable antibodies against mEpo in the sera of mice 90 days after injection with pVRmEpo, it is possible to readminister plasmid DNA by IM injection if repeated therapy or dose escalation is required.

The present invention discloses the construction and characterization of a novel plasmid vector that produces high level expression and secretion of erythropoietin (Epo) following IM injection into adult immunocompetent mice. A single IM injection of as little as 10 mg of this plasmid produced physiologically significant levels of mEpo in the systemic circulation of adult immunocompetent mice and resulted in significant elevations in hematocrits that were stable for at least 90 days. The injected plasmid DNA remained localized at the site of injection and the amount of Epo production (as reflected by the elevated hematocrits) was proportional to the dose of plasmid DNA injected. Thus, IM injection of plasmid DNA represents a feasible approach to the treatment of serum protein deficiencies.

As shown in detail hereinafter in the Examples, IM injection of as little as 10 mg of pVRmEpo (a novel plasmid expression vector, pVRmEpo, which directs high level production and secretion of mEpo from skeletal myocytes in vitro) into adult immunocompetent mice resulted in dose-dependent elevations in hematocrits that remained stable for at least 90 days. The increased hematocrits observed in the pVRmEpo-injected mice reflected persistent production of mEpo from the injected muscle and secretion of this protein into the systemic circulation. Finally, the injected DNA remained predominantly localized to muscle at the site of injection. The data disclosed herein represent the first demonstration of the delivery of physiologically significant levels of recombinant protein to the systemic circulation following the IM injection of a plasmid DNA expression vector.

The expression vector drives expression of the polynucleotide that encodes the particular gene product. Thus, the vector needs to contain those expression elements necessary for expression. For example, a polynucleotide of an expression vector of the present invention is preferably operatively associated or linked with an enhancer-promoter. A promoter is a region of a DNA molecule typically within about 100 nucleotide pairs in front of (upstream of) the point at which transcription begins. That region typically contains several types of DNA sequence elements that are located in similar relative positions in different genes. As used herein, the term "promoter" includes what is referred to in the art as an upstream promoter region or a promoter of a generalized RNA polymerase transcription unit.

Another type of transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from a transcription start site so long as the promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" or its grammatical equivalent means that a regulatory sequence element (e.g. an enhancer-promoter or transcription terminating region) is connected to a coding sequence in such a way that the transcription of that coding sequence is controlled and regulated by that enhancer-promoter. Means for operatively linking an enhancer-promoter to a coding sequence are well known in the art.

An enhancer-promoter used in an expression vector of the present invention can be any enhancer-promoter that drives expression in a host cell. By employing an enhancer-promoter with well known properties, the level of expression can be optimized. For example, selection of an enhancer-promoter that is active in specific cells (e.g., muscle cells) permits tissue or cell specific expression of the desired product. Still further, selection of an enhancer-promoter that is regulated in response to a specific physiological signal can permit inducible expression.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Enhancer-promoters and transcription-terminating regions are well known in the art. The selection of a particular enhancer-promoter or transcription-terminating region will depend, as is also well known the art, on the cell to be transformed.

The muscle cells can be transformed either in vivo or ex vivo. When transformed in vivo, the expression vector can be directly injected into muscle cells of the mammal. Alternately, the vector can be delivered to the muscle cells by infusing the vector into an artery or vein that perfuses the target muscle. Means for transforming smooth, cardiac and skeletal muscle in vivo are well known in the art. In a preferred embodiment, the vectors are directly injected into cardiac or skeletal muscle.

When transformed ex vivo, muscle cells are removed from the mammal, transformed ex vivo and the transformed muscle cells reimplanted into the primate. When ex vivo procedures are used, the use of skeletal muscle is preferred.

A process of the present invention is used to increase the circulating level of a gene product. As used herein, the term "increase" means to raise the circulating level above the pre-transformation level. Thus, the present process can be used to enhance levels above the normal physiological level of that gene product or can be used to correct abnormal deficiencies in the level of that product. Further, as shown hereinafter in the Examples, the circulating level of a gene product can be increased in a dose-dependent fashion. Preferably, the pre-transformation circulating levels can be increased at least 10 percent with use of the present process. Even more preferably, the circulating levels can be increased at least 20 percent, 50 percent, 100 percent or even greater. The data set forth hereinafter in the Examples also show that the physiological activity (e.g., hematocrit) of the gene product (e.g., erythropoietin) can also be increased with use of the present process.

The Examples that follow illustrate preferred embodiments of the present invention and are not limiting of the specification and claims in any way.

EXAMPLE 1

Plasmid Vectors pVRhEpo contains an 840 bp Not I human erythropoietin (hEpo) cDNA fragment from pAdEF1hEpo cloned into the Not I site of the plasmid vector, pVR1012(24). pVRmEpo contains a 620 bp Sal I/Bgl II murine erythropoietin cDNA fragment obtained by PCR of pAdEF1mEpo (25) with sense and antisense primers (5'-GGGGTCGACGGCGGGGAGATGGGGGTGCCCG [SEQ ID NO: 1], 5'-GGGAGATCTAGTTCACCTGTCCCCTCTCCTGC [SEQ ID NO:2]) and cloned into the Sal I and Bgl II sites of pVR1012. pVRbgal contains the bacterial lacZ gene cloned into the multiple cloning site (MCS) of pVR1012 and pVR1902 contains the canine factor IX cDNA cloned into the MCS of pVR1012.

Transfections —C2C12 myoblasts ($10^6$ cells in a 10 cm tissue culture dish) were transfected with 15 mg of pVRmEpo using the lipofectamine reagent (Gibco BRL, Gaithersburg, Md.). Approximately 16 hours later, the transfected cells were placed in fusion medium (DMEM, 2% horse serum, 1% penicillin/streptomycin) and the cells were allowed to fuse into myotubes overnight. Media was harvested at the times indicated after fusion and assayed for mEpo using a radioimmunoassay.

IM injection of plasmid DNA—Purified plasmid DNA was resuspended in sterile PBS -/- (Gibco BRL, Gaithersburg, Md.) at a concentration of 3 mg/ml. Mice were injected IM into the tibialis anterior or rectus femoris muscles with 50–100 μl of DNA solution per site containing 10–100 mg of DNA. Hematocrits were measured on blood collected by tail vein or orbital venipuncture.

Epo assays—Tissues were harvested from mice 90 days after injection with plasmid DNA and homogenized in approximately 1 ml of Epo specimen diluent buffer (R and D Systems, Minneapolis, Minn.), centrifuged at 10,000 X g for 10 minutes, and supernatants collected. Murine Epo levels were measured in cell culture supernatants, serum, and tissue lysates using a radioimmunoassay that is specific for mEpo.

PCR—Southern assays—Total cellular DNA was isolated from mouse tissues. For SCID mice, approximately 1 mg of total cellular DNA from each tissue was subject to the PCR using primers corresponding to sequences within the hEpo cDNA (5'-CCAGACCCCGAAGCATGG) (SEQ ID NO:3) and the pVR plasmid (5'-GGAAGACTTAAGGCAGCG) (SEQ ID NO:4). For CD-1 and BALB/c mice, approximately 100 ng of cellular DNA from each tissue was subjected to the PCR using primers corresponding to sequences within the mEpo cDNA (5'-GAAGTCAGGCTACGTAGACCACTG) (SEQ ID NO:5) and the pVR1012 plasmid (5'-GTCTGAGCAGTACTCGTTGC) (SEQ ID NO:6). The resulting PCR products were fractionated on a 1% agarose gel and analyzed by Southern blotting using a radiolabeled Bam H1/Pvu II fragment of the hEpo cDNA or a radiolabeled Bgl II/Sac I fragment of the mEpo cDNA as probes. All cellular DNA samples were also subjected to the PCR using primers specific for the cardiac troponin C (cTnC) gene and the products were visualized in ethidium-bromide stained agarose. PCR conditions were 35 cycles (94° C. for 1 min., 72° C. for 1 min.) followed by a 10 minute extension at 72° C.

EXAMPLE 2

In Vitro Analysis of pVRmEpo

In order to construct a plasmid expression vector that could program high level production and secretion of recombinant proteins from skeletal myofibers in vivo, the human (hEpo) and murine (mEpo) erythropoietin cDNAs were cloned into pVR1012, a plasmid vector which contains a eukaryotic expression cassette controlled by the CMV IE promoter, and the CMV IE 5' untranslated and intron A sequences followed by the bovine growth hormone polyadenylation signal. pVR1012 was used in these experiments because this plasmid backbone has been shown to program high level luciferase expression following IM injection into immunocompetent mice.

In initial experiments, C2C12 skeletal myoblasts were transfected with pVRmEpo and allowed to fuse into multinucleated myotubes. Culture supernatants from these transfected myotubes were assayed for mEpo at various times after transfection. C2C12 cells transiently transfected with pVRmEpo produced approximately 2000 mU/hr/$10^6$ cells of mEpo (4800 mU/ml X 10 ml/24 hours). Supernatants from control (pVRbgal-transfected) C2C12 cells did not contain detectable mEpo levels. Thus, pVRmEpo programmed high level mEpo expression and secretion following transfection into cultured skeletal myocytes. Similar high-level hEpo expression and secretion was observed following transfection of C2C 12 cells with pVRhEpo.

EXAMPLE 3

IM Injection of Epo Expression Vector DNA Produces Physiologically Significant Levels of Epo in the Systemic Circulation of Mice To determine whether IM injection of a plasmid Epo expression vector could produce physiologically significant levels of Epo in the systemic circulation of adult mice, adult SCID mice were injected IM with 300 mg of pVRhEpo or the control plasmid, pVR1012 which does not contain a cDNA insert. Hematocrits of the pVRhEpo-injected mice rose from pre-injection values of 48±1.2% to values of 68±2.4% within 14 days of injection and remained elevated at this level for the 90 day time course of the experiment. These elevated hematocrits were significantly different from those of control mice injected with identical amounts of pVR1012 (P <0.006). Injection of adult immunocompetent CD1 mice with 300 mg of pVRmEpo produced similar elevations in hematocrits (74±2.4% in the pVRmEpo-injected animals vs. 47±1% in control injected animals; P<0.01) which were also sustained over the 90 day time course of the experiment.

EXAMPLE 4

Elevated Serum and Muscle Epo Levels in the pVRmEpo-injected Mice

To demonstrate directly that the increased hematocrits observed in the pVRmEpo-injected mice reflected persistently elevated serum mEpo levels in these animals, serum mEpo levels were assayed 90 days after injection using a radioimmunoassay (RIA) that can detect mEpo. Serum mEpo levels in the pVRmEpo-injected animals were significantly elevated as compared to mEpo levels in serum from control mice (52 mU/ml in the pVRmEpo-injected mice vs. 8 mU/ml in the control mice; P<0.03). To determine the site of mEpo production in the pVRmEpo-injected mice, tissue lysates prepared from liver, kidney, and muscle at the site of IM injection were assayed for mEpo by RIA. Murine Epo levels in lysates from the pVRmEpo-injected muscle were significantly elevated as compared to levels in control uninjected muscle lysate (130 mU/ml in the pVRmEpo-injected muscle vs. 2 mU/ml in the uninjected muscle; P<0.0001). There were no significant differences in the mEpo levels detected in the other tissue lysates tested from the pVRmEpo-injected or uninjected animals. Thus, the elevated hematocrits observed in the pVRmEpo-injected animals reflected persistent production and secretion of recombinant mEpo from the pVRmEpo-injected muscle.

A dose-response relationship between the amount of DNA injected and the subsequent elevation in hematocrit—To determine directly if the level of polycythemia observed following IM injection of pVRmEpo was proportional to the amount of DNA injected, BALB/c mice were injected IM with 10, 100, or 300 mg of pVRmEpo, and hematocrits were measured during the 90 days following injection. IM injection of as little as 10 mg of pVRmEpo resulted in stable elevations in hematocrits from pre-injection values of 48±0.4% to post-injection levels of 64±3.3% at 45 days after injection. Injections of 100 or 300 mg of DNA caused further increases in hematocrits to levels of 79±3.3% at 45 days after injection which declined to 67±4.7% at 90 days after injection. The hematocrits observed in each treatment group were significantly elevated at each time point from those observed in control mice injected with 300 mg of pVR1012 (P<0.004). Thus, the observed levels of polycythemia were proportional to the amount of pVRmEpo DNA injected at least over the range of 10–100 mg of injected DNA.

Plasmid DNA remains localized at the site of IM injection—To determine the distribution of plasmid DNA following IM injection with pVRmEpo or pVRhEpo, mice were sacrificed 90 days after injection and total cellular DNA from a number of tissues was assayed for the presence of pVRmEpo DNA using a PCR assay that could detect as little as 0.00001 copies of the plasmid per cell. In both SCID mice injected with pVRhEpo and CD1 and BALB/c mice injected with pVRmEpo, plasmid DNA could be detected in lysates prepared from the injected muscle. In some animals, a barely detectable signal was also observed in the liver. Taken together with the studies data set forth above, the results show that the preponderance of plasmid DNA remained localized at the site of IM injection.

EXAMPLE 5

Long-Term Expression

Material and Methods Adenovirus Vectors. AdBgIII is an "empty" E1 - and E3-deleted RDAd that does not express a transgene (Barr et al., *Gene Ther.* 1, 51–58, 1994). AdmEpo is an E1- and E3-deleted RDAd containing the murine Epo cDNA under the transcriptional control of the elongation factor 1 (EF1) promoter and 4F2 heavy chain (4F2HC) first intron enhancer. The construction and characterization of this vector has been described previously (Tripathy et al., *Nature Med.* 2, 545–550, 1996). AdsEpo, an E1- and E3-deleted first generation replication-defective adenovirus vector containing the cynomolgus simian erythropoietin (sEpo) cDNA under the transcriptional control of the EF1 promoter and 4F2HC first intron enhancer was constructed as follows: PCR primers (5'-GGGGGGATCCGCACCTGGTCATCTGTCC-3'(SEQ ID NO:7) and (5'-GGGAAGCTTCCCGGCCAGGCGCGGAGATGG-3') (SEQ ID NO:8) were designed to amplify a 603 bp sEpo cDNA fragment from pMKE83 (obtained from American Type Culture Collection) with Hind III and Bam HI compatible ends. The resulting PCR product was subcloned into Hind III+Bam HI-digested pAdEF1 (Tripathy et al.,. $Proc.$ $Natl.$ $Acad.$ $Sci.$ $USA.$ 91, 11557–11561, 1994) to produce pAdsEpo. The fidelity of the sEpo cDNA PCR product was confirmed by dideoxy DNA sequence analysis. pAdsEpo was then used to generate the AdsEpo adenovirus by transfection of 293 cells as described previously (Tripathy et al., $Proc.$ $Natl.$ $Acad.$ $Sci.$ $USA,$ 91, 11557–11561, 1994). The resulting virus was plaque-purified 3 times prior to preparation of a master seed stock. All adenovirus preparations were produced by infection of 293 cells with master seed stocks that were free of detectable replication-competent helper virus as determined using a PCR assay (Tripathy et al., $Proc.$ $Natl.$ $Acad.$ $Sci.$ $USA,$ 91, 11557–11561, 1994). Adenoviruses were purified by centrifugation in CsCl density gradients, desalted by dialysis in storage buffer (10 mM Tris, pH 7.4, 1 mM $MgCl_2$, 10% glycerol) and frozen in aliquots at $-70°$ C. Virus titers were determined by plaque assay on 293 cells.

Intramuscular Injection of RDAd. For the mouse experiments, a total volume of 50 ml containing $10^8$ or $10^9$ pfu of AdBglII or AdmEpo was injected IM via a 26 gauge needle into a single site in the right tibialis anterior muscle of adult immunocompetent CD1 mice. For the monkey experiments, adult Cynomolgus monkeys were anesthetized with ketamine and atropine, intubated and ventilated with Halothane during adenoviral injections. The skin above the injection site was shaved and tattooed to mark the site of injection. The monkeys were then injected IM with a total dose of $4\times10^{11}$ pfu of AdBglII or AdsEpo (10 injections of 1 ml each of virus at a concentration of $4\times10^{10}$ pfu/ml into 10 different sites) or with $4\times10^{10}$ pfu of AdsEpo (2 injections of 1 ml each of virus at a concentration of $2\times10^{10}$ pfu/ml into 2 different sites). Buprenorphine was used over the following 48 hours to manage animal discomfort.

Hematocrits and Epo Assays. Blood was obtained from mouse tail veins by tail bleeds and monkey femoral veins by venipuncture. Hematocrits were determined by centrifugation of whole blood. mEpo assays were performed using a radioimmunoassay as described previously (Tripathy et al., $Nature$ $Med.$ 2, 545–550, 1996). sEpo assays were performed using the Quantikine IVD rhEpo ELISA kit (R&D Systems, Minneapolis, Minn.) according to the manufacturer's instructions.

Detection of Anti-adenoviral Antibodies. Titers of anti-adenoviral antibodies were determined by ELISA as described previously (Tripathy et al., $Nature$ $Med.$ 2, 545–550, 1996) except that peroxidase-conjugated rabbit anti-monkey IgG (Accurate chemical & Scientific, Westbury, N.Y.) was used instead of alkaline phosphatase-conjugated goat anti-mouse IgG.

EXAMPLE 6

Dose-response Relationship of Long-term Epo Expression Following IM Injection of Mice with AdmEpo Previous studies have demonstrated stable dose-dependent elevations of hematocrits and serum Epo levels following a single IM injection of $10^7$, $10^8$, or $10^9$ pfu of Epo-encoding RDAd in immuno-compromised SCID mice (Tripathy et al., $Proc.$ $Natl.$ $Acad.$ $Sci.$ $USA$ 91, 11557–11561, 1994). To determine if a similar dose-response relationship existed in adult immunocompetent CD1 mice, and whether the persistence of Epo transgene expression was dependent upon the dose of virus administered, we injected adult CD 1 mice IM with $10^8$ or $10^9$ pfu of AdmEpo or with $10^9$ pfu of a control virus, AdBgl II, that lacks the mEpo transgene. As expected, mice injected with the AdBgl II control virus showed no significant change in their hematocrits from the normal pre-injection values of 52±1.5%. In contrast, mice injected with $10^9$ pfu AdmEpo displayed significant elevations in hematocrits from pre-injection values of 49±0.9% to levels of 81±3% 84 days after injection (p<0.0001). Interestingly, unlike SCID mice which displayed stable elevations in hematocrits after injection of $10^7$, $10^8$ or $10^9$ pfu of AdEpo vectors (Tripathy et al.,. $Proc.$ $Natl.$ $Acad.$ $Sci.$ $USA,$ 91, 11557–11561, 1994), immunocompetent CD1 mice injected with $10^8$ pfu of AdmEpo showed only a transient rise in hematocrit to 65±1.6% at 14 days after injection followed by a return to baseline values of approximately 51±1.0% by 21 days post-injection. In additional experiments using a range of virus doses, we demonstrated that it is necessary to inject mice with at least $7\times10^8$ pfu of AdmEpo to produce persistent Epo expression in the blood for 90 days. Increasing doses of AdmEpo between $7\times10^8$ pfu and $3\times10^9$ pfu resulted in dose-dependent elevations in hematocrits in CD1 mice.

To ensure that the observed changes in hematocrits accurately reflected changes in serum Epo levels in these mice, a radioimmunoassay was used to directly measure serum Epo levels in animals from each of the three experimental groups. Mice injected with $10^8$ pfu of AdmEpo displayed transient elevations of serum Epo levels to 13 mU/ml one week after injection followed by a return to baseline levels (<5 mU/ml) at 14 days post-injection. In contrast, serum Epo levels in the mice injected with $10^9$ pfu AdmEpo peaked at 91 mU/ml one week after injection, then declined to 26 mU/ml at 14 days post injection with persistence of this level throughout the remainder of the 84 day experiment. Thus, the changes in hematocrits observed in these mice reflect persistently elevated serum Epo levels. Because the half-life of Epo in the serum is approximately 4 hours, these results also demonstrated the persistence of Epo expression for at least 84 days following a single IM injection of $10^9$ pfu of AdmEpo. When taken together, these experiments demonstrated that unlike SCID mice, which displayed dose-dependent elevations in hematocrits following injection with as little as $10^7$ pfu of Epo-encoding vectors (Tripathy et al., $Proc.$ $Natl.$ $Acad.$ $Sci.$ $USA,$ 91, 11557–11561, 1994), the immunocompetent CD1 animals required higher doses of virus to produce sustained levels of transgene-encoded Epo expression in the systemic circulation.

EXAMPLE 7

Persistent Expression of Physiological Levels of mEpo in the Systemic Circulation of Mice for More Than One Year Following a Single IM Injection of AdmEpo Previous studies have demonstrated persistent elevations in hematocrits in CD1 mice for at least 112 days following a single IM injection of 1–$3\times10^9$ pfu of AdmEpo. Given the potential difficulties with re-administration of adenovirus vectors following an initial infection (due to the generation of neutralizing antibodies) (Barr et al., $Gene$ $Ther.$ 2, 151–155, 1995; Kass et al., *Gene Ther.* 1,395–402, 1994; Mastrangeli et al., *Hum. Gene Ther.* 7,79–87, 1996; Tripathy et al., *Nature Med.* 2, 545–550, 1996; Yang et al. 1996), it was of interest to determine the longevity of transgene expression following a single IM injection of AdmEpo. Moreover, given the differences in immune responses in different strains of inbred mice, it was important to evaluate the persistence of transgene expression in different mouse strains. Accordingly, adult C57BL/6, C3H, CD1, and BalbC mice were injected once IM with $2-3\times10^9$ pfu of AdmEpo and hematocrits were followed serially for one year. All strains of mice demonstrated persistent elevations in hematocrits which were stable for at least one year. In contrast, control mice injected TM with a vector lacking the mEpo transgene displayed no significant changes in hematocrits over the time course of the experiment. These experiments show that a single IM injection of an RDAd encoding a self transgene (mEpo) can result in stable expression of physiological levels of Epo in multiple strains of mice for at least one year.

EXAMPLE 8

Elevations of Hematocrits and Serum Epo Levels Following a Single IM Injection of AdsEpo in Cynomolgus Monkeys The results of the mouse experiments described above demonstrated long-term Epo expression in a small rodent model following a single IM injection of an RDAd encoding a self transgene (mEpo). However, before this approach could be considered for use in human gene therapy, it was important to confirm its efficacy and safety in a large animal model, preferably a primate.

It is essential to use RDAd encoding self transgenes in pre-clinical trials in order to avoid cellular and humoral immune responses directed against foreign transgene products (Tripathy et al. 1996a). Accordingly, for trials in non-human primates, AdsEpo, an E1- and E3-deleted RDAd containing the cynomolgus simian Epo cDNA under the transcriptional control of the EF1 promoter and 4F2 HC first intron enhancer was made. AdsEpo was shown to program high level expression of sEpo following infection of C2C12 myoblasts in vitro. Adult Cynomolgus monkeys were injected once IM with $4\times10^{10}$ or $4\times10^{11}$ pfu of AdsEpo. These doses were calculated based upon the ratios of the body weights of mice and monkeys: the average weight of a mouse is 25 g and the weight of our monkeys was approximately 5 kg. Therefore, a dose of $2\times10^9$ pfu in a mouse would be equivalent to a dose of $4\times10^{11}$ in a monkey while a dose of $2\times10^8$ in a mouse is equivalent to a dose of $4\times10^{10}$ in a monkey. A control monkey received a single IM injection of $4\times10^{11}$ pfu of the AdBgl II virus.

The control monkey which was injected with the AdBglII virus did not demonstrate a significant change in hematocrit from the pre-injection values of 40%. The monkey injected with $4\times10^{10}$ pfu of AdsEpo showed a rise in hematocrit to a peak level of 61% at one month post-injection and a subsequent gradual decline to 49% by day 84, the end of the experiment. In contrast, the monkey injected with $4\times10^{11}$ pfu of AdsEpo displayed an elevation of hematocrit to 71% by 56 days post injection. In order to avoid cerebral thrombotic events, the protocol specified weekly phlebotomy of all animals with hematocrits of =65%. Accordingly, this animal was phlebotomized 50 ml (approximately 10% of its blood volume) at days 56, 63, 70, and 77. Despite this repeated phlebotomy, the animal demonstrated stable hematocrits of =65% throughout the remainder of the experiment. Measurement of serum Epo levels at the end of the experiment were in accord with the observed hematocrits: the animal injected with $4\times10^{10}$ pfu of AdsEpo whose hematocrit was mildly elevated had a serum Epo level of 4.4±0.3 mU/ml, 13-fold elevated over the control level of 0.34±0.15 mU/ml. In contrast, the animal injected with $4\times10^{11}$ pfu of AdsEpo had a serum Epo level of 52.7±2 mU/ml, 150-fold higher than the animal injected with AdBglII ($p<0.0001$).

EXAMPLE 9

Safety of AdsEpo Injection in Non-human Primates

Intravenous and inhaled administration of first generation adenovirus vectors have been associated with hepatic toxicity and pulmonary inflammation, respectively (Brody et al., *Hum. Gene Ther.* 5, 821–836, 1994; Yang et al., *Proc. Natl. Acad. Sci. USA* 91, 4407–4411, 1994; Yang et al., *J. Immunol.* 155, 2564–2570, 1995). To assess the safety of IM injection of AdsEpo, chest X-rays, serum chemistries, hematologic profiles, and clotting parameters were monitored in the monkeys receiving IM injections of both AdsEpo and AdBglII. In addition, all three animals underwent necropsy at the end of the experiment which was performed by an independent pathologist. Chest x-rays were normal in all animals at 1 and 4 weeks after infection as were lung histologies at necropsy. Thus, there was no evidence of pulmonary toxicity in any of the animals. The monkey that received $4\times10^{11}$ pfu of AdBglII displayed a rise in ALT to 2–4 fold over the normal range between 1 and 4 weeks after injection. This elevated serum ALT level returned to normal by the end of the 84 day experiment and was not accompanied by elevations of GGT, bilirubin, or alkaline phosphatase. Moreover, no significant elevations in LFTs were seen in either of the monkeys injected with AdsEpo. Consistent with these findings, none of the monkeys displayed liver pathology at necropsy 84 days after injection. However, it should be noted that these studies might have missed hepatic inflammation occurring at earlier times after injection, an important consideration given previous findings that hepatic inflammation is maximal 7–14 days after IV injection of first generation RDAd (Yang et al. 1994). Nevertheless, the lack of significant elevations of liver enzymes throughout the experiment when taken together with the normal liver histologies seen 84 days after infection show that IM injection of RDAd is not associated with significant long-term hepatotoxicity. Histological examination of muscle at the site of adenovirus injection did not reveal significant pathology 84 days after. Consistent with this observation, serum CPKs were normal in all three animals at 1 and 12 weeks after injection. Thus, the protocol was not associated with detectable muscle toxicity. With the exception of a single elevated platelet count seen in the monkey injected with $4\times10^{10}$ of AdsEpo, abnormalities in serum chemistries, hematologic profiles (aside from elevated hematocrits) or clotting parameters were not detected in any of the animals. In both animals injected with AdsEpo, necropsy revealed an increase in the bone marrow cellularity of the erythroid series. There were no other significant findings in any of the animals on necropsy. Taken together, these experiments demonstrated the relative safety of IM injection of AdsEpo, at least up to the dose of $4\times10^{11}$ pfu in a 5 kg monkey.

EXAMPLE 10

Anti-adenoviral Antibody Titers Following AdsEpo Injection

Previous studies in rodents have demonstrated that mice injected IM or IV with first-generation RdAd develop high titers of neutralizing antibodies that preclude repeated administration of the viral vector for at least 60–90 days (Barr et al., *Gene Ther.* 2, 151–155, 1995; Kass et al.,. *Gene Ther.* 1, 395–402, 1994; Mastrangeli et al., *Hum. Gene Ther.* 7, 79–87, 1996; Tripathy et al., *Nature Med.* 2, 545–550, 1996; Yang et al., *Gene Ther.* 3, 137–144, 1996). Indeed, an IM injection of $10^9$ PFU of AdmEpo into mice that had received $10^8$ pfu of AdmEpo 9 months previously was unable to produce further increases in hematocrits. To determine the extent of the anti-adenoviral humoral immune response following IM injection of Cynomolgus monkeys with AdsEpo, sera from all three animals were assayed for the presence of anti-adenoviral antibodies by ELISA. In the animal injected with $4\times10^{11}$ pfu of AdBgl II or AdsEpo, the titer of anti-adenoviral antibodies increased 200-fold from pre-injection values. In contrast, the animal injected with $4\times10^{10}$ pfu of AdsEpo displayed a 20-fold rise in titer of anti-adenoviral antibodies. Thus, based upon small numbers of primates, there appeared to be a dose-dependent humoral response to the injected adenovirus.

What is claimed is:

1. A process for increasing the circulating levels of a self protein in the blood stream of an immunocompetent animal which comprises delivering an adenoviral vector in vivo to muscle cells of said animal by intramuscular injection in an amount sufficient to obtain expression of and increase the circulating level of said self protein in the bloodstream of said animal for a period greater than about 30 days, wherein said self protein is erytbropoietin or a growth hormone.

2. The process of claim 1 wherein the animal is a primate.

3. The process of claim 2 wherein the primate is a human.

4. The process of claim 1 wherein the adenoviral vector is a replication defective adenoviral vector.

5. The process of claim 1 wherein the self protein is human erythropoietin.

6. The process of claim 1 wherein the circulating level of the self protein is increased for a period of time greater than about 60 days.

7. The process of claim 1 wherein the circulating level of the self protein is increased for a period of time greater than about 90 days.

8. The process of claim 1 wherein the circulating level of the self protein is increased for a period of time greater than about 120 days.

9. The process of claim 1 wherein the circulating level of the self protein is increased for a period of time ranging from about 90 days to about 365 days.

10. The process of claim 1 wherein the muscle cells are cardiac muscle cells or skeletal muscle cells.

11. A process for increasing the circulating levels or a self protein in the blood stream of an immunocompetent animal which comprises transforming muscle cells of said animal ex vivo with an adenoviral vector encoding a self protein to thereby produce transformed muscle cells, wherein said self protein is erythropoietin or a growth hormone, and further wherein said self protein undergoes secretion, diffusion, or transport to the circulation upon expression in vivo; and delivering said transformed muscle cells by intramuscular injection to said animal in an amount sufficient to obtain expression of and increase the circulating level of said self protein in the bloodstream of said animal for a period greater than about 30 days.

12. The process of claim 11 wherein the animal is a primate.

13. The process of claim 12 wherein the primate is a human.

14. The process of claim 11 wherein the adenoviral vector is a replication-defective adenoviral vector.

15. The process of claim 11 wherein the self protein is human erythropoietin.

16. The process of claim 11 wherein the circulating level of the self protein is increased for a period of time greater than about 60 days.

17. The process of claim 11 wherein the circulating level of the self protein is increased for a period of time greater than about 90 days.

18. The process of claim 11 wherein the circulating level of the self protein is increased for a period of time greater than about 120 days.

19. The process of claim 11 wherein the circulating level of the self protein is increased for a period of time ranging from about 90 days to about 365 days.

20. The process of claim 11 wherein the muscle cells are cardiac muscle cells or skeletal muscle cells.

21. The process of claim 11, wherein said immunocompetent animal is being treated with an immunosuppressant.

22. The process of claim 1, wherein said immunocompetent animal is being treated with an immunosuppressant.

23. The process of claim 1 wherein the self protein is human growth hormone.

24. The process of claim 11 wherein the self protein is human growth hormone.

* * * * *